United States Patent
Hori et al.

(10) Patent No.: US 6,175,047 B1
(45) Date of Patent: Jan. 16, 2001

(54) RUTHENIUM METATHESIS CATALYST AND METHOD FOR PRODUCING OLEFIN REACTION PRODUCT BY METATHESIS REACTION USING THE SAME

(75) Inventors: Yoji Hori; Yukiharu Iwaya; Tsutomu Hashimoto; Toshimitsu Hagiwara, all of Hiratsuka (JP)

(73) Assignee: Takasago International Corporation, Tokyo (JP)

( * ) Notice: Under 35 U.S.C. 154(b), the term of this patent shall be extended for 0 days.

(21) Appl. No.: 09/219,351

(22) Filed: Dec. 23, 1998

(30) Foreign Application Priority Data

Dec. 26, 1997 (JP) .................................................. 9-370275
May 15, 1998 (JP) .................................................. 10-170447

(51) Int. Cl.[7] .............................. C07C 6/04; C07C 6/06; B01J 31/02; B01J 31/12
(52) U.S. Cl. ........................ 585/645; 585/643; 585/644; 502/150; 502/152; 502/155; 502/162
(58) Field of Search .................................. 502/150, 152, 502/155, 162; 585/643, 644, 645

(56) References Cited

U.S. PATENT DOCUMENTS 5,342,909 * 8/1994 Grubbs et al. .................... 526/171
5,917,071 * 6/1999 Grubbs et al. .................... 556/21

FOREIGN PATENT DOCUMENTS

WO 97/06185 * 2/1997 (WO) .

* cited by examiner

*Primary Examiner*—Elizabeth D. Wood
(74) *Attorney, Agent, or Firm*—Kubovcik & Kubovcik

(57) ABSTRACT

The invention has an object of safely and simply preparing a large amount of a ruthenium metathesis catalyst, which is used as a catalyst for a carbon-carbon bond formation using, particularly, a metathesis reaction. The metathesis catalyst has the following complex composition (A) or (B). The composition (A) includes $RuX^1{}_2(arene)(PR^1R^2R^3)$ and $R^4CHX^2{}_2$, $R^5C\equiv CH$ or $R^4CHX^2$ and a reducing agent, wherein $X^1$ and $X^2$ respectively are a halogen atom; arene is a hydrocarbon having a benzene ring; $R^1$, $R^2$ and $R^3$, which may be the same or different, respectively are an alkyl group having 1–8 carbon atoms, a cycloalkyl group having 3–8 carbon atoms or an optionally substituted aryl group, wherein the substituent group is an alkyl group having 1–8 carbon atoms, an alkoxy group having 1–8 carbon atoms, an alkylamino group having 1–8 carbon atoms or a halogen atom; $R^4$ is an alkyl group which has 1–8 carbon atoms and may have an ether bond or an ester bond, an optionally subsituted aryl group, wherein the substituent group is a halogen atom or a hydroxyl group; or cycloalkyl group having 3–8 carbon atoms; and $R^5$ is an optionally substituted alkyl group which has 1–8 carbon atoms and may have an ether bond or an ester bond, wherein the substituent group is a halogen atom or a hydroxyl group, an aryl group or a cycloalkyl group having 3–8 carbon atoms. The composition B includes $[RuX^1{}_2(arene)]_2$, $PR^1R^2R^3$, $R^5C\equiv CH$ or $R^4CHX^2$ and a reducing agent, wherein $X^1$, arene, $R^1$, $R^2$, $R^3$, $R^4$ and $R^5$ are the same as defined above.

5 Claims, No Drawings

RUTHENIUM METATHESIS CATALYST AND METHOD FOR PRODUCING OLEFIN REACTION PRODUCT BY METATHESIS REACTION USING THE SAME

BACKGROUND OF THE INVENTION

1. Field of the Invention

The present invention relates to a novel ruthenium metathesis catalyst and to a method for producing an olefin by using the ruthenium metathesis catalyst, and, more particularly, to a ruthenium metathesis catalyst used as a catalyst for a carbon-carbon bond formation reaction using various organic synthetic reactions, especially, a metathesis reaction and to a method for producing cyclic olefins, internal olefins or polyolefins.

2. Prior Art

Many transition metal complexes have been used as catalysts for organic synthetic reactions. Among these reactions, a metathesis reaction of an olefin by using a transition metal complex as the catalyst has been variously studied (R. H. Grubbs, W. Tumas, Science, 1989, 243, pp 907–915).

This reaction is conventionally used for synthesizing bioactive natural substances such as civetone, $D^{9,12}$-capnellane or 9-tricosene by using a tungsten type catalyst ($WCl_6/EtAlCl_2$ or $WCl_6/Cp_2TiMe_2$, wherein Et represents an ethyl group, Me a methyl group and Cp a cyclopentadienyl group) or a titanium type catalyst ($Cp_2Ti(Cl)CH_2AlMe_2$) (Grubbs et al. Acc. Chem. Res. 1995, 28, pp446–452). The metathesis reaction is generally inferior in selectivity of type of reaction, yield, and stability to a variety of functional groups.

Recently, there has been a report that ring closing metathesis of nonconjugated diene and enone proceed using a molybdenum carbon complex catalyst in a highly selective and efficient manner (R. H. Grubbs et al. Acc. Chem. Res. 1995, 28, pp 446–452). This catalyst is, however, very unstable to many functional groups, oxygen and moisture.

For this, a ruthenium carbene complex which is relatively stable to air and moisture has been developed (WO 93/20111, WO 96/04289, WO 97/06185, F. Ozawa et al. 44th Symposium on Organometallic Chemistry, Japan. Abstracts, 1997, pp 74–75). This catalyst is effective for a ring closing metathesis reaction of nonconjugated dienes, ring opening metathesis polymerization of cyclic olefins, and the like. However, many steps are required to prepare this catalyst.

In order for the catalyst to be prepared in short steps, the catalyst is used in situ to carry out the ring opening metathesis polymerization of norbornene and cyclooctenes (A. F. Noels et al., J. Chem. Soc., Chem. Commun., 1995, pp 1127–1128; Macromolecules, 1997, 30, pp3127–3136). However, because these methods use unstable compounds (for example, diazo compounds), the production of a large amount of the catalyst is made with difficulty in actual industrialization. Hence the metathesis reaction using such a catalyst cannot be utilized on an industrial scale.

SUMMARY OF THE INVENTION

Accordingly, an object of the present invention is to provide a ruthenium metathesis catalyst which can be produced in a large amount safely and simply by using a stable precursor and compounding this precursor in the system and also to provide a method for producing cyclic olefins, internal olefins or polyolefins efficiently in a short period of time by using this catalyst to carry out the metathesis reaction and ring opening metathesis polymerization of olefins.

The object of the present invention can be attained by the provision of a metathesis catalyst comprising:

a ruthenium compound represented by the formula (1);

$$RuX^1_2(arene)(PR^1R^2R^3) \tag{1}$$

and a compound selected from the group consisting of;
a dihalogeno compound represented by the formula (2);

$$R^4CHX^2_2 \tag{2}$$

or
a terminal alkyne represented by the formula (3);

$$R^5C\equiv CH \tag{3}$$

wherein $X^1$ and $X^2$ respectively represent a halogen atom; arene represents a hydrocarbon having a benzene ring; $R^1$, $R^2$ and $R^3$, which may be the same or different, respectively represent an alkyl group having 1–8 carbon atoms, a cycloalkyl group having 3–8 carbon atoms or an optionally substituted aryl group (wherein the substituent group is an alkyl group having 1–8 carbon atoms, an alkoxy group having 1–8 carbon atoms, an alkylamino group having 1–8 carbon atoms or a halogen atom); $R^4$ represents an alkyl group which has 1–8 carbon atoms and may have an ether bond or an ester bond or an aryl group which may have a substituent group (wherein the substituent group is a halogen atom or a hydroxyl group or a cycloalkyl group having 3–8 carbon atoms); and $R^5$ represents an alkyl group which has 1–8 carbon atoms and may have a substituent group and an ether bond or an ester bond (wherein the substituent group is a halogen atom or a hydroxyl group), an aryl group or a cycloalkyl group having 3–8 carbon atoms.

According to another aspect of the present invention, there is provided a metathesis catalyst comprising:
a ruthenium compound represented by the formula (4);

$$[RuX^1_2(arene)]_2 \tag{4}$$

a phosphine represented by the formula (5);

$$PR^1R^2R^3 \tag{5}$$

and
a terminal alkyne represented by the formula (3);

$$R^5C\equiv CH \tag{3}$$

wherein $X^1$ represents a halogen atom; arene represents a hydrocarbon having a benzene ring; $R^1$, $R^2$ and $R^3$, which may be the same or different, respectively represent an alkyl group having 1–8 carbon atoms, a cycloalkyl group having 3–8 carbon atoms or an optionally substituted aryl group (wherein the substituent group is an alkyl group having 1–8 carbon atoms, an alkoxy group having 1–8 carbon atoms, an alkylamino group having 1–8 carbon atoms or a halogen atom); and $R^5$ represents an alkyl group which has 1–8 carbon atoms and may have a substituent group and an ether bond or an ester bond (wherein the substituent group is a halogen atom or a hydroxyl group), an aryl group or a cycloalkyl group having 3–8 carbon atoms.

In a preferred embodiment, the metathesis catalyst may comprise a dihalogeno compound represented by the formula (2) and a reducing agent instead of the terminal alkyne;

$$R^4 CHX^2{}_2 \qquad (2).$$

According to a further aspect of the present invention, there is provided a method for producing a cyclic olefin, an internal olefin or a polyolefin by using the metathesis catalyst.

DESCRIPTION OF THE PREFERRED INVENTION

A first ruthenium metathesis catalyst according to the present invention comprises a ruthenium compound represented by the formula (1):

$$RuX^1{}_2(arene) (PR^1R^2R^3) \qquad (1)$$

and a dihalogeno compound represented by the formula (2);

$$R^4CHX^2{}_2 \qquad (2)$$

or comprises a ruthenium compound represented by the formula (1):

$$RuX^1{}_2(arene) (PR^1R^2R^3) \qquad (1)$$

and a terminal alkyne represented by the formula (3):

$$R^5C\equiv CH \qquad (3)$$

Specific examples of $X^1$ in the formula $RuX^1{}_2$ (arene) $(PR^1R^2R^3)$ which is a first component constituting the catalyst include chlorine, bromine and iodine. Preferred examples of "arene" include benzene and benzene having a substituent group. Preferable examples of the substituent group include alkyl groups or alkoxy groups having 1–4 carbon atoms. Specifically, preferable arenes are benzene, p-cymene, methoxybenzene, and hexamethylbenzene.

Examples of the groups represented by $R^1$, $R^2$ and $R^3$ in the formula $(PR^1R^2R^3)$ include, as the alkyl group having 1–8 carbon atoms, a methyl group, ethyl group, propyl group, isopropyl group, butyl group, 1-methylpropyl group, pentyl group, 2-ethylpropyl group, 1-methylbutyl group, hexyl group, 1-methylpentyl group, 1-methylhexyl group and 1-methylheptyl group; as the cycloalkyl group having 3–8 carbon atoms, a cyclopropyl group, cyclobutyl group, cyclopentyl group, cyclohexyl group, cycloheptyl group and cyclooctyl group; and, as the aryl group which may have a substituent group, a phenyl group, 2-methylphenyl group, 4-methylphenyl group, 2,6-dimethylphenyl group, 4-biphenyl group, 4-methoxyphenyl group, 4-dimethylaminophenyl group, 4-chlorophenyl group, 1-naphthyl group and 2-naphthyl group.

Specific examples of the phosphine include triisopropylphosphine, tri(butane-2-yl)phosphine, tri(pentane-3-yl)phosphine, tri(hexane-2-yl)phosphine, tri(heptane-2-yl)phosphine, tri(octane-2-yl)phosphine, diisopropylphenylphosphine, di(butane-2-yl)phenylphosphine, di(pentane-2-yl)phenylphosphine, di(pentane-3-yl)phenylphosphine, di(hexane-2-yl)phenylphosphine, di(heptane-2-yl)phenylphosphine, di(octane-2-yl)phenylphosphine, isopropyldiphenylphosphine, butane-2-yldiphenylphosphine, pentane-2-yldiphenylphosphine, pentane-3-yldiphenylphosphine, hexane-2-yldiphenylphosphine, heptane-2-yldiphenylphosphine, octane-2-yldiphenylphosphine, tricyclopropylphosphine, tricyclobutylphosphine, tricyclopentylphosphine, tricyclohexylphosphine, tricycloheptylphosphine, tricyclooctylphosphine, dicyclopropylphenylphosphine, dicyclobutylphenylphosphine, dicyclopentylphenylphosphine, dicyclohexylphenylphosphine, dicycloheptylphenylphosphine, dicyclooctylphenylphosphine, cyclopropyldiphenylphosphine, cyclobutyldiphenylphosphine, cyclopentyldiphenylphosphine, cyclohexyldiphenylphosphine, cycloheptyldiphenylphosphine and cyclooctyldiphenylphosphine.

The ruthenium complex represented by the aforementioned formula (1) can be obtained by, for example, the method described in J. C. S. Dalton Trans., 233(1974). Specifically, dichloro(p-cymene)triphenylphosphine ruthenium ($RuCl_2$(p-cymene) $PPh_3$) is obtained by refluxing di-$\mu$-chlorobis[(p-cymene)chlororuthenium] ($[RuCl_2$(p-cymene)$]_2$) and triphenylphosphine in an organic solvent.

The present invention is characterized in that the aforementioned ruthenium complex is used. Stated in another way, a ruthenium complex containing, for example, cyclooctadiene in place of arene does not have the same effect as in the present invention.

Specific examples of 1,1-dihalides represented by the formula (2) which is a second component constituting the aforementioned catalyst include 1,1-dihalogenoalkanes such as ethylidene chloride, ethylidene bromide and ethylidene iodide; dihalogenoalkyl aromatic compounds such as benzal chloride, benzal bromide and benzal iodide; and dihalogeno fatty acid esters such as methyl dichloroacetate, methyl dibromoacetate, methyl diiodoacetate, ethyl dichloroacetate, ethyl dibromoacetate and ethyl diiodoacetate. In the present invention, the 1,1-dihalides may be used in an amount of two equivalent moles to the ruthenium complex represented by the formula (1). The 1,1-dihalides can serve as a reaction solvent.

The dihalides are commercially available or can be prepared by known methods.

The second component constituting the catalyst may be a terminal alkyne represented by the formula (3). Specific examples of the terminal alkyne include aromatic type acetylenes such as phenyl acetylene, 4-methylphenylacetylene, 4-chlorphenylacetylene and 3-phenyl-1-propyne; aliphatic type acetylenes such as 1-pentyne, 1-hexyne, 1-heptyne, 1-octyne, 1-decyne, 3,3-dimethyl-1-butyne and 5-chloro-1-pentyne; alcohols such as propargyl alcohol, 3-butyne-2-ol, 2-methyl-3-butyne-2-ol and 3-butyne-1-ol; esters such as 2-propynyl acetate, 2-methyl-3-butyne-2-yl acetate and methyl acetylene carboxylate; carbonates such as propargyl methyl carbonate; and ethers such as propargyl methyl ether.

The amount of the terminal alkyne used in the present invention may be two equivalent moles to the ruthenium complex represented by the formula (1). The terminal alkyne can serve as a reaction solvent. These terminal alkynes are commercially available or can be prepared by known methods.

The first metathesis catalyst comprises a combination of the ruthenium compound (1) and the dihalogeno compound (2) or a combination of the ruthenium compound (1) and the terminal alkyne (3). This metathesis catalyst can be readily obtained by placing the ruthenium complex (1) and the dihalogeno compound (2) or the terminal alkyne (3) in a reaction vessel in which air is replaced with inert gas, e.g., nitrogen, and by stirring these compounds in a solvent.

Given as examples of materials used as the solvent are halogenated organic solvents such as methylene chloride, methylene bromide, 1,2-dichloroethane and chlorobenzene; aromatic hydrocarbon solvents such as benzene, toluene and xylene; esters such as ethyl acetate, butyl acetate and methyl benzoate; dimethylformamide, dimethylsulfoxide, dioxane and tetrahydrofuran.

In the preparation of the catalyst, it is desirable that the amount of the ruthenium complex (1) contained in the solvent be 0.001 to 1 molar concentration.

The second metathesis catalyst comprises a ruthenium compound represented by the formula (4):

$$[RuX^1_2(arene)]_2 \quad (4)$$

a phosphine represented by the formula (5):

$$PR^1R^2R^3 \quad (5)$$

and a terminal alkyne represented by the formula (3):

$$R^5C{\equiv}CH \quad (3)$$

wherein $X^1$, arene, $R^1$, $R^2$, $R^3$ and $R^5$ are the same as defined above.

X and "arene" in the ruthenium compound represented by the formula (4) which is the first component constituting the second metathesis catalyst are compounds such as those described above.

The ruthenium complex represented by the aforementioned formula (4) can be obtained by, for example, the method described in Can. J. Chem., Vol 50, 3063 (1972). Specifically, di-μ-chlorobis[(p-cymene)chlororuthenium ([RuCl$_2$(p-cymene)]$_2$) is obtained by refluxing ruthenium chloride and α-phellandrene in ethanol.

Specific examples of the ruthenium complex include [RuCl$_2$(benzene)]$_2$, [RuCl$_2$(p-cymene)]$_2$, [RuCl$_2$(hexamethylbenzene)]$_2$, [RuCl$_2$(methoxybenzene)]$_2$, [RuBr$_2$(benzene)]$_2$, [RuBr$_2$(p-cymene)]$_2$, [RuBr$_2$(hexamethylbenzene)]$_2$, [RuBr$_2$ methoxybenzene)]$_2$, [RuI$_2$(benzene)]$_2$, [RuI$_2$(p-cymene)]$_2$, [RuI$_2$(hexamethylbenzene)]$_2$ and [RuI$_2$(methoxybenzene)]$_2$.

The phosphine (5) which is the second component constituting the second metathesis catalyst includes compounds such as those already mentioned.

It is advantageous from the standpoints of reactivity and economy that the phosphine is used in the present invention in an amount of an equivalent mol or more of the ruthenium complex shown in the above formula (4), specifically, 1.6–2 equivalent moles or more to the ruthenium complex.

The terminal alkyne (3) which is the third component constituting the second metathesis catalyst also includes compounds such as those as already mentioned.

The metathesis catalyst comprising the ruthenium complex (4), phosphine (5) and terminal alkyne (3) can be easily prepared by placing these components in a reaction vessel in which air is replaced with inert gas such as nitrogen and by stirring the mixture in a solvent.

Examples of the solvent used in the above process include halogenated organic solvents such as methylene chloride, methylene bromide, 1,2-dichloroethane and chlorobenzene; aromatic hydrocarbon solvents such as benzene, toluene and xylene; esters such as ethyl acetate, butyl acetate and methyl benzoate; dimethylformamide, dimethylsulfoxide, dioxane and tetrahydrofuran.

In the preparation of the catalyst, it is desirable that the amount of the ruthenium complex (4) be 0.001 to 1 molar concentration.

A dihalogeno compound represented by the formula (2) and a reducing agent may be used in place of the terminal alkyne:

$$R^4CHX^2_2 \quad (2).$$

The dihalogeno compound may contain a reducing agent. Particularly desirable reducing agents are metal reducing agents. Specific examples of the metal reducing agent include powders, granules and ribbons of lithium, sodium, potassium, magnesium, calcium, aluminum, tin, zinc, iron, and alloys containing these metals. Among these compounds, preferred metals are magnesium, aluminum, zinc and iron. The amount of the metal used in the present invention is 2–100 equivalents, preferably 5–50 equivalents and more preferably 10–30 equivalents to the ruthenium complex.

The metathesis catalyst of the present invention which is prepared in the above manner has an extremely high catalytic activity and can be used as a catalyst for preparing a metathesis reaction product from a metathesis reaction substrate.

As the substrate for the metathesis reaction, any substrate may be used insofar as it can be used in metathesis reactions known prior to the present invention. Specific examples of the reaction substrate include terminal olefins represented by the formula (6):

$$CH_2{=}CHR^7 \quad (6)$$

wherein $R^7$ represents a hydrogen atom, an alkyl group having 1–20 carbon atoms, an alkenyl group and an aryl group, where these groups may have a substituent group including a hydroxy group, a carboxy group, a keto group, a silyl group, an alkoxy group, an aryloxy group, an amino group, a halogen atom, an aryl group and groups having an ester or amide bond; internal olefins represented by the formula (7):

$$R^8CH{=}CHR^9 \quad (7)$$

wherein $R^8$ and $R^9$ respectively represent a hydrogen atom, an alkyl group having 1–20 carbon atoms, an alkenyl group and an aryl group, where these groups may have a substituent group including a hydroxy group, a carboxy group, a keto group, a silyl group, an alkoxy group, an aryloxy group, an amino group, a halogen atom, an aryl group and groups having an ester or amide bond; and cyclic olefins represented by the formula (8):

(8)

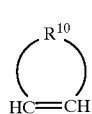

wherein $R^{10}$ represents an alkylene group, an alkenylene group and an arylene group and these groups have 1–20 carbon atoms and may have an oxygen atom and a nitrogen atom or a substituent group including a hydroxy group, a carboxy group, a keto group, a silyl group, an alkoxy group, an aryloxy group, an amino group, a halogen atom, an aryl group and groups having an ester or amide bond.

The above substrates of olefins may be used either independently or in combinations of two or more. It is desirable to use a method which determines a combination of these substrate materials based on the chemical structure of an object olefinic product. A cross-metathesis reaction, ring opening metathesis polymerization or the like may be utilized.

Though no particular limitation is imposed on metathesis reaction products in the present invention, typical metathesis reaction products are exemplified as follows.

Given as examples of terminal olefins are hydrocarbons such as ethylene, propylene, 1-butene, 1-pentene, 1-hexene, 1-octene, 1-decene, styrene, 4-chlorostyrene and 4-methoxystyrene; alcohols such as 2-propene-1-ol (allyl alcohol), 4-pentene-2-ol, 5-hexene-1-ol, 2-methyl-6-heptene-2-ol, 9-decene-1-ol, p-decene-2-ol and 10-undecene-1-ol; esters such as 2-propenyl acetate, 5-hexene-1-yl acetate, 9-decene-1-yl acetate, 10-undecene-1-yl acetate, methylacrylate, methyl 3-butenoate, methyl 9-decenoate and methyl 10-undecenoate and acids such as 9-decenoic acid and 10-undecenoic acid.

Given as examples of internal olefins are hydrocarbons such as 2-butene, 2-pentene, 3-hexene, 3-heptene, 4-octene, 5-decene and 9-octadecene; alcohols such as 2-butene-1,4-diol; acids such as 9-octadecene-1,18-dicarboxylic acid and 10-eicosene-1,20-dicarboxylic acid; and esters such as dimethyl 9-octadecene-1,18-dicarboxylate and dimethyl 10-eicosene-1,20-dicarboxylate.

Given as examples of cyclic olefins are hydrocarbons such as cyclopentene, cyclohexene and cyclooctene; esters such as diethyl 3-cyclopentene-1, 1-dicarboxylate; and lactones such as 10-tetradecene-14-olide, 10-pentadecene-15-olide, 4-pentadecene-15-olide and 10-eicosene-20-olide.

Given as examples of the polyolefin are poly(cyclooctene), poly(norbornene) and poly(7-oxanorbornene).

In order to carry out a metathesis reaction using the catalyst of the present invention, the aforementioned metathesis catalyst and a desired solvent are stirred for about 10 minutes to one hour at 0° C. to 140° C. and preferably at room temperature to 80° C. Then, the reaction substrate is directly introduced into the solution containing the catalyst. Alternatively, each component comprised of the metathesis catalyst and the reaction substrate may be mixed at the same time to carry out a metathesis reaction in a solvent. Also, a part of the components comprised of the metathesis catalyst may be first mixed and the remaining components of the catalyst added. Moreover, first the reaction substrate may be introduced into a solvent and then the components of the catalyst added.

As the solvent used in this process, it is advantageous to use the same solvent as in the preparation of the catalyst. However, it need not be the same one.

The temperature of the metathesis reaction is 0° C. to 140° C. and preferably room temperature to 80° C. The reaction time is 30 minutes to 40 hours.

The amount of the ruthenium complex is 0.001 to 50 mol %, preferably 0.01 to 30 mol % and more preferably 0.05 to 20 mol % based on the reaction substrate.

EXAMPLES

The present invention will be explained in detail by way of examples and comparative examples which are not intended to be limiting of the present invention. In the following examples, the properties of the prepared compounds were measured using the following instruments. The results of Examples 1 to 5 and Examples 7 and 8 are shown in Table 1.

$^1$H-NMR spectrum: DRX-500 type instrument (manufactured by Bruker, Inc.)

Internal standard material: tetramethylsilane $^{31}$P-NMR spectrum: DRX-500 type instrument (manufactured by Bruker, Inc.)

External standard material: 85% phosphoric acid

Molecular weight: D-2520 GPC Integrater (manufactured by Hitachi, Ltd.)

Reference Example

Synthesis of dichloro (p-cymene) tricyclohexylphosphine ruthenium 15 ml of a methylene chloride solution containing 1.567 g (5.59 mmol) of tricyclohexylphosphine was added dropwise to 20 ml of a methylene chloride solution containing 1.86 g (3.0 mmol) of di-$\mu$-chlorobis[(p-cymene)chlororuthenium] in a nitrogen stream in an ice-cooled condition and then the reaction solution was stirred at room temperature for one hour in a nitrogen stream to concentrate the solution so that its volume is reduced to about 15 ml. To the concentrate was added 70 ml of hexane and the resulting solution was allowed to stand for 2 hours. The precipitated solid was filtered and the precipitate was washed with hexane, followed by drying the precipitate by using a vacuum pump to obtain 2.89 g of an object material (yield: 82.3%).

$^1$H-NMR(CD$_2$Cl$_2$) δ: 1.1(d, 6H, J=7 Hz), 1.85 (s, 3H), 2.78(sept, 1H, J=6.9 Hz), 4.99(d, 2H), 5.19(d, 2H), 7.35–7.39(m, 6H), 7.40–7.42(m, 3H), 7.77–7.81(m, 6H)

$^{31}$P-NMR(CD$_2$Cl$_2$) δ: 25.77(s)

Example 1

Synthesis of diethyl 3-cyclopentene-1,1-dicarboxylate

A 5 ml flask was charged with 0.293 g (1.22 mmol) of diethyl diallyl malonate, 0.036 g (0.061 mmol) of dichloro (p-cymene)tricyclohexylphosphine ruthenium, 1.5 ml of toluene and 0.006 ml (0.061 mmol) of methyl dichloroacetate and the mixture was stirred at 80° C. for 2.5 hours in a nitrogen stream (conversion rate: 89.3%). A solvent was distilled and the residue was subjected to silica gel column chromatography (toluene) to obtain 0.224 g of an object material (yield: 76.6%).

$^1$H-NMR(CDCl$_3$) δ: 1.24(t, 6H, J=7.2 Hz), 3.00 (s, 4H), 4.19(q, 4H, J=7.2 Hz), 5.60(s, 2H)

Example 2

Synthesis of diethyl 3-cyclopentene-1,1-dicarboxylate

A 10 ml flask was charged with 0.539 g (2.246 mmol) of diethyl diallyl malonate, 0.066 g (0.112 mmol) of dichloro (p-cymene)tricyclohexylphosphine ruthenium, 3 ml of toluene and 0.015 ml (0.112 mmol) of benzal chloride and the mixture was stirred at 80° C. for 3 hours in a nitrogen stream to obtain an object material the conversion was 61.4% and the yield was 54.6%.

Example 3

Synthesis of diethyl 3-cyclopentene-1,1-dicarboxylate

The same procedure as in Example 1 was carried out except that 0.0067 ml (0.061 mmol) of phenylacetylene was used instead of methyl dichloroacetate and the stirring was continued for 18 hours, to obtain an object material. The conversion was 95.5% and the yield was 80.9%.

Example 4

Synthesis of diethyl 3-cyclopentene-1,1-dicarboxylate

The same procedure as in Example 1 was carried out except that 0.0059 g (0.061 mmol) of propargyl acetate was used instead of methyl dichloroacetate and the stirring was continued for 20 hours, to obtain an object material. The conversion was 91.8% and the yield was 66.0%.

Example 5

Synthesis of diethyl 3-cyclopentene-1,1-dicarboxylate

The same procedure as in Example 1 was carried out except that 0.0059 ml (0.061 mmol) of propargyl bromide was used instead of methyl dichloroacetate and the stirring was continued for 20 hours, to obtain an object material. The conversion was 61.1% and the yield was 57.3%.

Example 6

Synthesis of polyoctene by ring opening metathesis polymerization of cyclooctene 0.025 g (0.043 mmol) of dichloro(p-cymene)tricyclohexylphosphine ruthenium, 1 ml of toluene, 0.0043 ml (0.043 mmol) of methyl dichloroacetate and 2.8 ml of (21.5 mmol) of cyclooctene were mixed and stirred for 18 hours in a nitrogen stream. The reaction product was dissolved in 5 ml of methylene chloride, which was introduced into 150 ml of methanol to reprecipitate thereby producing an object material containing 1.90 g of polyoctene in a yield of 80.2%. The weight average molecular weight and number average molecular weight of the polyoctene were 81,200 and 68,900 respectively.

$^1$H-NMR(CDCl$_3$) δ: 1.00–1.75(m, 10H), 1.75–2.10 (m, 2H), 5.20–5.50 (m, 2H).

Example 7

Synthesis of diethyl 3-cyclopentene-1,1-dicarboxylate

A 5 ml flask was charged with 0.056 g (0.2 mmol) of tricyclohexylphosphine, 0.06 g (0.1 mmol) of di-μ-chlorobis((p-cymene)chlororuthenium, 5 ml of toluene, 0.02 ml (0.2 mmol) of phenylacetylene and 0.91 g (3.79 mmol) of dimethyl diallyl malonate and the mixture was stirred at 80° C. for 23 hours in a nitrogen stream. The conversion rate was 93.0% and the yield was 89.0%.

Example 8

Synthesis of diethyl 3-cyclopentene-1,1-dicarboxylate

The same procedure as in Example 7 was carried out except that 0.02 ml (0.2 mmol) of 2-methyl-3-butyne-2-ol was used instead of phenylacetylene and the stirring was continued for 20 hours to obtain an object material. The conversion was 79.8% and the yield was 57.8%.

Example 9

Synthesis of 3-cyclopentenyl benzoate

A 100 ml flask was charged with 0.53 g (1.9 mmol) of tricyclohexylphosphine, 0.62 g (1.0 mmol) of di-μ-chlorobis((p-cymene)chlororuthenium), 50 ml of toluene, 0.22 ml (2 mmol) of phenylacetylene and 8.28 g (38.3 mmol) of 1,6-heptadiene-4-yl benzoate and the mixture was stirred at 80° C. for 22 hours in a nitrogen stream. The reaction solution was washed with an aqueous 1% sodium hydroxide solution and saturated brine in this order, followed by drying using magnesium sulfate anhydride. A solvent was distilled and the residue was subjected to vacuum distillation (73–74° C./5 mmHg) to obtain 5.00 g of an object material in a yield of 69.4%.

$^1$H-NMR(CDCl$_3$) δ: 2.51, 2.59 (dd, 2H), 2.82, 2.90 (dd, 2H), 5.59–5.65 (m, 1H), 5.77 (s, 2H), 7.38–7.58(m, 3H), 8.00–8.05(m, 2H)

Example 10

Synthesis of polyoctene by ring opening metathesis polymerization of cyclooctene 0.070 g (0.25 mmol) of tricyclohexylphosphine, 0.065 g (0.125 mmol) of di-μ-chlorobis((p-cymene)chlororuthenium, 1 ml of toluene, 0.0255 g (0.25 mmol) of phenylacetylene and 2.76 g (25 mmol) of cyclooctene were mixed and stirred for 22 hours in a nitrogen stream. The solidified reaction product was dissolved in chloroform, which was introduced into 1.0 l of methanol to reprecipitate thereby producing an object material containing 1.77 g of polyoctene in a yield of 64.2%. The weight average molecular weight and number average molecular weight of the polyoctene were 909,000 and 529,000 respectively.

$^1$H-NMR(CDCl$_3$) δ: 1.00–1.75(m, 10H), 1.75–2.10 (m, 2H), 5.20–5.50 (m, 2H).

Comparative Example 1

A flask was charged with 0.078 g (0.28 mmol) of tricyclohexylphosphine, 0.078 g (0.28 mmol) of dichloro-1,5-cyclooctadiene ruthenium, 3.3 ml of toluene, 0.03 ml (0.28 mmol) of phenylacetylene and 0.36 g (1.50 mmol) of diethyl diallyl malonate and the mixture was stirred at 80° C. for 4 hours in a nitrogen stream, but no reaction took place at all.

Comparative Example 2

A flask was charged with 0.059 g (0.21 mmol) of tricyclohexylphosphine, 0.055 g (0.21 mmol) of ruthenium trichloride trianhydride, 4 ml of toluene, 0.023 ml (0.21 mmol) of phenylacetylene and 0.27 g (1.13 mmol) of diethyl diallyl malonate and the mixture was stirred at 80° C. for 4 hours in a nitrogen stream, but no reaction took place at all.

Example 11

Preparation of a catalyst

A 50 ml of flask was charged with 0.056 g (0.2 mmol) of tricyclocyclohexylphosphine, 0.06 g (0.1 mmol) of di-μ-chlorobis((p-cymene)chlororuthenium), 10 ml of toluene, 0.13 g (1.99 mmol) of a zinc powder and 0.024 ml (0.2 mmol) of benzal chloride and the mixture was stirred at 80° C. for one hour in a nitrogen stream to prepare a catalyst.

Example 12

Synthesis of diethyl 3-cyclopentene-1,1-dicarboxylate

A 50 ml flask was charged with 0.056 g (0.2 mmol) of tricyclohexylphosphine, 0.06 g (0.1 mmol) of di-μ-chlorobis ((p-cymene)chlororuthenium, 10 ml of toluene, 0.13 g (1.99 mmol) of a zinc powder, 0.024 ml (0.2 mmol) of benzal chloride and 0.24 g (1 mmol) of diethyl diallyl malonate and the mixture was stirred at 80° C. for 4 hours in a nitrogen stream. The conversion was 91.5%. The obtained insoluble substance was filtered. A solvent was distilled and the residue was subjected to silica gel column chromatography (toluene). The resulting product was distilled under reduced pressure to obtain 0.15 g of an object material (yield: 65.4%).

Example 13

Synthesis of diethyl 3-cyclopentene-1,1-dicarboxylate

The same procedure as in Example 12 was carried out except that 0.05 g (1.85 mmol) of an aluminum powder was used instead of 0.13 g of the zinc powder and 0.021 ml (0.2 mmol) of methyl dichloroacetate instead of benzal chloride and the stirring was continued for two hours, to obtain an object material, the conversion was 96.5% and the yield was 93.4%.

Example 14

Synthesis of diethyl 3-cyclopentene-1,1-dicarboxylate

The same procedure as in Example 12 was carried out except that 0.05 g (2.06 mmol) of a magnesium powder was used instead of the zinc powder and the stirring was continued for 16 hours, to obtain an object material. The conversion was 97.6% and the yield was 91.2%.

Example 15

Synthesis of diethyl 3-cyclopentene-1,1-dicarboxylate

The same procedure as in Example 14 was carried out except that 0.11 g (1.97 mmol) of an iron powder was used instead of the magnesium powder, to obtain an object material the conversion was 92.4% and the yield was 90.3%.

Example 16

Synthesis of diethyl 3-cyclopentene-1,1-dicarboxylate

The same procedure as in Example 12 was carried out except that 0.05 g (1.85 mmol) of an aluminum powder was used instead of 0.13 g of the zinc powder and the amount of diethyl diallyl malonate was changed from 0.24 g to 0.96 g (4 mmol), the amount of methyl dichloroacetate was changed from 0.021 ml to 0.063 ml and the amount of toluene was changed from 10 ml to 5 ml, to obtain an object material. The conversion was 93.5% and the yield was 71.1%.

Example 17

Synthesis of diethyl 3-cyclopentene-1,1-dicarboxylate

The same procedure as in Example 13 was carried out except that the amount of diethyl diallyl malonate was changed from 0.24 g to 0.96 g (4 mmol), the amount of methyl dichloroacetate was changed from 0.021 ml to 0.063 ml and 5 ml of ethyl acetate was used instead of 10 ml of toluene, to obtain an object material. The conversion was 68.0% and the yield was 43.5%.

Example 18

Synthesis of diethyl 3-cyclopentene-1,1-dicarboxylate

The same procedure as in Example 12 was carried out except that 0.021 ml of methyl dichloroacetate was used instead of 0.024 ml of benzal chloride and the stirring was continued for 3 hours, to obtain an object material. The conversion was 95.4% and the yield was 86.1%.

Example 19

Synthesis of diethyl 3-cyclopentene-1,1-dicarboxylate

The same procedure as in Example 12 was carried out except that 0.05 g (2.06 mmol) of an aluminum powder was used instead of 0.13 g of the zinc powder and the stirring was continued for 17 hours, to obtain an object material. The conversion was 79.6% and the yield was 75.2%.

Example 20

Synthesis of diethyl 3-cyclopentene-1,1-dicarboxylate

The same procedure as in Example 12 was carried out except that 10 ml of methylene chloride was used instead of 10 ml of toluene and the stirring was continued at room temperature for 16 hours, to obtain an object material. The conversion was 99.0% and the yield was 97.0%.

Example 21

Synthesis of diethyl 3-cyclopentene-1,1-dicarboxylate

The same procedure as in Example 12 was carried out except that 0.098 g of di-$\mu$-iodobis ((p-cymene) iodoruthenium was used instead of 0.06 g of di-$\mu$-chlorobis ((p-cymene)chlororuthenium and the stirring was continued for 16 hours, to obtain an object material. The conversion was 63.0% and the yield was 51.3%.

Example 22

Synthesis of diethyl 3-cyclopentene-1,1-dicarboxylate

The same procedure as in Example 12 was carried out except that 0.05 g of di-$\mu$-chlorobis ((benzene) chlororuthenium) was used instead of 0.06 g of di-$\mu$-chlorobis((p-cymene)chlororuthenium) and the stirring was continued for 3 hours, to obtain an object material. The conversion was 97.7% and the yield was 86.2%.

Example 23

Synthesis of diethyl 3-cyclopentene-1,1-dicarboxylate

The same procedure as in Example 12 was carried out except that 0.093 g of 1,5-bis(dicyclohexylphosphino) pentane (hereinafter abbreviated as "di-CyPPn") was used instead of 0.056 g of tricyclohexylphosphine and the stirring was continued for 6 hours, to obtain an object material. The conversion was 63.5% and the yield was 57.9%.

Example 24

Synthesis of diethyl 3-cyclopentene-1,1-dicarboxylate

The same procedure as in Example 12 was carried out except that 0.055 g (0.2 mmol) of dicyclohexylphenyl phosphine was used instead of 0.056 g of tricyclohexylphosphine and the stirring was continued for 5.5 hours, to obtain an object material. The conversion was 47.1% and the yield was 37.5%.

Example 25

Synthesis of diethyl 3-cyclopentene-1,1-dicarboxylate

The same procedure as in Example 12 was carried out except that 10 ml of xylene was used instead of 10 ml of toluene and the stirring was continued at 140° C. for one hour, to obtain an object material. The conversion was 91.0% and the yield was 48.5%.

Example 26

Synthesis of diethyl 3-cyclopentene-1,1-dicarboxylate

The same procedure as in Example 12 was carried out except that 10 ml of chlorobenzene was used instead of 10 ml of toluene, 0.05 g of an aluminum powder instead of 0.13 g of a zinc powder and 0.021 ml of methyl dichloroacetate instead of 0.024 ml of benzal chloride, and the stirring was continued for 4 hours, to obtain an object material. The conversion was 96.3% and the yield was 60.8%.

Example 27

Synthesis of 6-dodecene 0.98 g (3.5 mmol) of tricyclohexylphosphine, 1.07 g (1.75 mmol) of di-$\mu$-chlorobis((p-cymene)chlororuthenium), 40 ml of toluene, 0.875 g (32.4 mmol) of an aluminum powder, 1.11 ml (10.5 mmol) of methyl dichloroacetate and 20 ml (142 mmol) of 1-heptene were blended and the mixture was stirred at 80° C. for 6 hours in a nitrogen stream. The insoluble substance was filtered and the filtrate was washed with an aqueous 1% sodium hydroxide solution (50 ml, two times). The organic layer was separated and washed with water and saturated brine in this order, followed by drying using magnesium sulfate anhydride. A solvent was distilled and the residue was subjected to vacuum distillation (71° C./5 mmHg) to obtain 4.26 g of 6-dodecene in a yield of 35.2%.

$^1$H-NMR(CDCl$_3$) δ: 0.88 (t, 6H, J=6.6 Hz), 1.22–1.37 (m, 12H), 1.90–2.08(m, 4H), 5.35–5.41 (m, 2H)

Example 28

Synthesis of 10-tetradecene-14-olide (1) Synthesis of 4-pentenyl 10-undecenoate A flask was charged with 10 g (116 mmol) of 4-pentenol, 200 ml of methylene chloride, 18.33 g (232 mmol) of pyridine and the mixture was ice-cooled. To the mixture was added dropwise 80 ml of a methylene chloride solution containing 23.51 g (116 mmol) of 10-undecenoyl chloride. The resulting mixture was stirred for 30 minutes and then at room temperature for 3 hours. The insoluble substance was filtered. 5% hydrochloric acid was added to the filtrate to separate an organic layer. The organic layer was washed with an aqueous saturated sodium bicarbonate solution and water in this order, followed by drying using magnesium sulfate anhydride. After the drying, a solvent was distilled and the residue was subjected to vacuum distillation (121–123° C./2 mmHg) to obtain 25.3 g of an object material in a yield of 86.4%.

The result of $^1$H-NMR(CDCl$_3$) of the above reaction solution is as follows:

$^1$H-NMR(CDCl$_3$) δ: 1.29–1.39(m, 10H), 1.58–1.64 (m, 2H), 1.69–1.76(m, 2H), 2.01–2.07(m, 2H), 2.09–2.15(m, 2H), 2.29(t, 2H), 4.08(t, 2H), 4.91–5.06(m, 4H), 5.76–5.86 (m, 2H)

(2) Synthesis of 10-tetradecene-14-olide 0.05 g of tricyclohexylphosphine, 0.06 g (0.1 mmol) of di-$\mu$-chlorobis ((p-cymene)chlororuthenium), 10 ml of toluene, 0.05 g (1.85 mmol) of an aluminum powder, 0.252 g (1 mmol) of 4-pentenyl 10-undecenoate and 0.021 ml (0.2 mmol) of methyl dichloroacetate were blended and the mixture was stirred at 80° C. for 16 hours in a nitrogen stream. A solvent was distilled and the residue was refined by silica gel column chromatography (toluene/ethyl acetate= 10/1) to obtain 0.09 g of an object material (yield: 40%). The result of $^1$H-NMR of the above reaction solution is as follows:

$^1$H-NMR(CDCl$_3$) δ: 1.29–1.36(m, 10H), 1.60–1.71(m, 4H), 1.95–2.08(m, 4H), 2.27–2.34(m, 2H), 4.04–4.12(m, 2H), 5.37–5.43(m, 2H)

Example 29

Synthesis of polycyclooctene by ring opening metathesis polymerization of cyclooctene 0.028 g (0.1 mmol) of tricyclohexylphosphine, 0.03 g (0.05 mmol) of di-$\mu$-chlorobis((p-cymene)chlororuthenium, 2 ml of toluene, 0.027 g (1.0 mmol) of an aluminum powder and 0.021 ml (0.2 mmol) of methyl dichloroacetate were mixed and stirred at 80° C. for 2 hours in a nitrogen stream. The solidified reaction product was dissolved in chloroform, which was introduced into 1.0 l of methanol to reprecipitate thereby producing an object material containing 4.84 g of polycyclooctene at a yield of 88%. The weight average molecular weight and number average molecular weight of the polycyclooctene were 1,229,000 and 706,000 respectively. The result of $^1$H-NMR of the object material is as follows:

$^1$H-NMR(CDCl$_3$) δ:1.00–1.75(m, 10H), 1.75–2.10 (m, 2H), 5.20–5.50 (m, 2H).

Table 1 shows the results of Examples 1 to 8 and Table 2 shows the results of Examples 12 to 26.

TABLE 1

| Ex. | Ru complex | Phosphine | aditive | Temp. (° C.) | Time(h) rate | Conversion (%) | Yield (%) |
|---|---|---|---|---|---|---|---|
| 1 | RuCl$_2$(p-cymene) (PCy$_3$) | | Cl$_2$CHCOOCH$_3$ | 80 | 2.5 | 89.3 | 76.6 |
| 2 | RuCl$_2$(p-cymene) (PCy$_3$) | | PhCHCl$_2$ | 80 | 3 | 61.4 | 54.6 |
| 3 | RuCl$_2$(p-cymene) (PCy$_3$) | | PhCCH | 80 | 18 | 95.5 | 80.9 |
| 4 | RuCl$_2$(p-cymene) (PCy$_3$) | | CH$_3$COOCH$_2$CCH | 80 | 20 | 91.8 | 66.0 |
| 5 | RuCl$_2$(p-cymene) (PCy$_3$) | | BrCH$_2$CCH | 80 | 20 | 61.1 | 57.3 |
| 7 | [RuCl$_2$(p-cymene)]$_2$ | PCy$_3$ | PhCCH | 80 | 23 | 93.0 | 89.0 |
| 8 | [RuCl$_2$(p-cymene)]$_2$ | PCy$_3$ | (CH$_3$)$_2$C(OH)CCH | 80 | 20 | 79.8 | 57.8 |

TABLE 2

| Ex. | Ru complex | Phosphine | Metal reducing agent | R$^4$CHX$_2$ | Temp. (° C.) | Time (h) | Conversion rate (%) | Yield (%) |
|---|---|---|---|---|---|---|---|---|
| 12 | [RuCl$_2$(p-cymene)]$_2$ | PCy$_3$ | Zn | PhCHCl$_2$ | 80 | 4 | 91.5 | 65.4 |
| 13 | [RuCl$_2$(p-cymene)]$_2$ | PCy$_3$ | Al | Cl$_2$CHCO$_2$Me | 80 | 2 | 96.5 | 93.4 |
| 14 | [RuCl$_2$(p-cymene)]$_2$ | PCy$_3$ | Mg | PhCHCl$_2$ | 80 | 16 | 97.6 | 91.2 |
| 15 | [RuCl$_2$(p-cymene)]$_2$ | PCy$_3$ | Fe | PhCHCl$_2$ | 80 | 16 | 92.4 | 90.3 |
| 16 | [RuCl$_2$(p-cymene)]$_2$ | PCy$_3$ | Al | Cl$_2$CHCO$_2$Me | 80 | 4 | 93.5 | 71.1 |
| 17 | [RuCl$_2$(p-cymene)]$_2$ | PCy$_3$ | Al | Cl$_2$CHCO$_2$Me | 80 | 4 | 68.0 | 43.5 |
| 18 | [RuCl$_2$(p-cymene)]$_2$ | PCy$_3$ | Zn | Cl$_2$CHCO$_2$Me | 80 | 3 | 95.4 | 86.1 |
| 19 | [RuCl$_2$(p-cymene)]$_2$ | PCy$_3$ | Al | PhCHCl$_2$ | 80 | 17 | 79.6 | 75.2 |
| 20 | [RuCl$_2$(p-cymene)]$_2$ | PCy$_3$ | Zn | PhCHCl$_2$ | r.t. | 17 | 99.0 | 97.0 |
| 21 | [RuI$_2$(p-cymene)]$_2$ | PCy$_3$ | Zn | PhCHCl$_2$ | 80 | 16 | 63.0 | 51.3 |
| 22 | [RuCl$_2$(benzene)]$_2$ | PCy$_3$ | Zn | PhCHCl$_2$ | 80 | 3 | 97.7 | 86.2 |
| 23 | [RuCl$_2$(p-cymene)]$_2$ | di-CyPPn | Zn | PhCHCl$_2$ | 80 | 6 | 63.5 | 57.9 |
| 24 | [RuCl$_2$(p-cymene)]$_2$ | Pcy$_2$Ph | Zn | PhCHCl$_2$ | 80 | 5.5 | 47.1 | 37.5 |
| 25 | [RuCl$_2$(p-cymene)]$_2$ | PCy$_3$ | Zn | PhCHCl$_2$ | 140 | 1 | 91.0 | 48.5 |
| 26 | [RuCl$_2$(p-cymene)]$_2$ | PCy$_3$ | Al | Cl$_2$CHCO$_2$Me | 80 | 4 | 96.3 | 60.8 |

Comparative Example 3

The same procedure as in Example 12 was carried out except that tricyclohexylphosphine was not used and the stirring was continued for 4 hours. However, the conversion was 0%.

Comparative Example 4

The same procedure as in Example 12 was carried out except that the zinc powder was not used and the stirring was continued for 4 hours. However, the conversion was 0%.

Comparative Example 5

The same procedure as in Example 12 was carried out except that benzal chloride was not used and the stirring was continued for 4 hours. However, the conversion was 0%.

Comparative Example 6

The same procedure as in Example 12 was carried out except that benzal chloride and the zinc powder were not used and the stirring was continued for 4 hours. However, the conversion was 35.2% and the yield was 2.9%.

The results of Comparative Examples 1 to 4 and Example 1 are shown in Table 3.

Comparative Example 7

Synthesis of diethyl 3-cyclopentene-1,1-dicarboxylate

A 50 ml flask was charged with 0.056 g (0.2 mmol) of tricyclohexylphosphine, 0.056 g (0.2 mmol) of dichloro-1, 5-cyclooctadiene ruthenium, 10 ml of toluene, 0.13 g (1.99 mmol) of a zinc powder, 0.24 g (1 mmol) of diethyl diallyl malonate and 0.024 ml (0.2 mmol) of benzal chloride and the mixture was stirred at 80° C. for 17 hours in a nitrogen stream. The conversion was 8.8% and the yield was 2.7%.

Comparative Example 8

Synthesis of diethyl 3-cyclopentene-1,1-dicarboxylate

A 50 ml flask was charged with 0.056 g (0.2 mmol) of tricyclohexylphosphine, 0.026 g (0.1 mmol) of ruthenium chloride, 10 ml of toluene, 0.13 g (1.99 mmol) of a zinc powder, 0.24 g (1 mmol) of diethyl diallyl malonate and 0.024 ml (0.2 mmol) of benzal chloride and the mixture was stirred at 80° C. for 4 hours in a nitrogen stream. The conversion and the yield were very low.

TABLE 3

| | Ru complex | Phosphine | Metal reducing agent | R²CHX₂ | Temp. (° C.) | Time (h) | Conversion rate (%) | Yield (%) |
|---|---|---|---|---|---|---|---|---|
| Example 12 | [RuCl₂(p-cymene)]₂ | PCy₃ | Zn | PhCHCl₂ | 80 | 4 | 91.5 | 65.4 |
| Comparative Example 3 | [RuCl₂(p-cymene)]₂ | | Zn | PhCHCl₂ | 80 | 4 | 0 | 0 |
| Comparative Example 4 | [RuCl₂(p-cymene)]₂ | PCy₃ | | PhCHCl₂ | 80 | 4 | 0 | 0 |
| Comparative Example 5 | [RuCl₂(p-cymene)]₂ | PCy₃ | Zn | | 80 | 4 | 0 | 0 |
| Comparative Example 6 | [RuCl₂(p-cymene)]₂ | PCy₃ | | | 80 | 4 | 35.2 | 2.9 |

According to the present invention, a catalyst capable of promoting a metathesis reaction efficiently can be prepared safely and simply. In the present invention, a variety of metathesis reaction products can be prepared by selecting olefins as a substrate, which is industrially very advantageous.

What is claimed is:

1. A metathesis catalyst comprising:

a ruthenium compound represented by formula (1);

$$RuX^1{}_2(arene)(PR^1R^2R^3) \quad (1)$$

and a compound selected from the group consisting of;

a dihalogeno compound represented by formula (2);

$$R^4CHX^2{}_2 \quad (2)$$

and a terminal alkyne represented by formula (3);

$$R^5C{\equiv}CH \quad (3)$$

wherein $X^1$ and $X^2$ respectively represent a halogen atom; arene represents a hydrocarbon having a benzene ring; $R^1$, $R^2$ and $R^3$, which may be the same or different, respectively represent an alkyl group having 1–8 carbon atoms, a cycloalkyl group having 3–8 carbon atoms or an optionally substituted aryl group, wherein the substituent group is an alkyl group having 1–8 carbon atoms, an alkoxy group having 1–8 carbon atoms, an alkylamino group having 1–8 carbon atoms or a halogen atom; $R^4$ represents an alkyl group which has 1–8 carbon atoms and may have an ether bond or an ester bond, or represents an optionally substituted aryl group, wherein the substituent group is a halogen atom, a hydroxyl group or cycloalkyl group having 3–8 carbon atoms; and $R^5$ represents an optionally substituted alkyl group which has 1–8 carbon atoms and may have an ether bond or an ester bond, wherein the substituted group is a halogen atom or a hydroxyl group, an aryl group or a cycloalkyl group having 3–8 carbon atoms.

2. A method for producing an olefin, said method comprising effecting a metathesis reaction of an olefin substrate in a solution into which a metathesis catalyst is added, said metathesis catalyst being the metathesis catalyst recited in claim 1.

3. A method for producing an olefin reaction product according to claim 2, wherein said olefin substrate is a terminal olefin.

4. A method for producing an olefin reaction product according to claim 2, wherein said olefin substrate is an internal olefin.

5. A method for producing an olefin reaction product according to claim 2, wherein said olefin substrate is a cyclic olefin.

* * * * *